(12) United States Patent
Azizian et al.

(10) Patent No.: US 11,998,282 B2
(45) Date of Patent: Jun. 4, 2024

(54) SYSTEMS AND METHODS FOR TELEOPERATED CONTROL OF AN IMAGING INSTRUMENT

(71) Applicant: INTUITIVE SURGICAL OPERATIONS, INC., Sunnyvale, CA (US)

(72) Inventors: Mahdi Azizian, Santa Clara, CA (US); Jonathan M. Sorger, Belmont, CA (US); Oliver J. Wagner, Mountain View, CA (US); Andrew C. Waterbury, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 826 days.

(21) Appl. No.: 16/470,050

(22) PCT Filed: Dec. 15, 2017

(86) PCT No.: PCT/US2017/066843
§ 371 (c)(1),
(2) Date: Jun. 14, 2019

(87) PCT Pub. No.: WO2018/112424
PCT Pub. Date: Jun. 21, 2018

(65) Prior Publication Data
US 2020/0015910 A1 Jan. 16, 2020

Related U.S. Application Data
(60) Provisional application No. 62/435,399, filed on Dec. 16, 2016.

(51) Int. Cl.
*A61B 34/20* (2016.01)
*A61B 17/34* (2006.01)
(Continued)

(52) U.S. Cl.
CPC .......... *A61B 34/20* (2016.02); *A61B 17/3403* (2013.01); *A61B 34/35* (2016.02);
(Continued)

(58) Field of Classification Search
CPC ..... A61B 34/20; A61B 17/3403; A61B 34/35; A61B 1/00193; A61B 2017/3413;
(Continued)

(56) References Cited

U.S. PATENT DOCUMENTS

| 6,445,943 B1 | 9/2002 | Ferre et al. |
| 7,170,285 B2 | 1/2007 | Spratte |

(Continued)

FOREIGN PATENT DOCUMENTS

WO  WO-2014005225 A1  1/2014

OTHER PUBLICATIONS

Dimaio S.P. et al., "Robot-Assisted Laparoscopic Ultrasound", Information Processing in Computer-Assisted Interventions, Lecture Notes in Computer Science, Springer-Verlag, vol. 6135, 2010, pp. 67-80.

(Continued)

*Primary Examiner* — Thomas McEvoy
(74) *Attorney, Agent, or Firm* — Haynes & Boone, LLP

(57) ABSTRACT

A medical imaging system comprises a teleoperated assembly including a medical instrument, a first imaging instrument, a second imaging instrument, a tracking fixture, and a processor. The first imaging instrument generates a first image of a field of view of the first imaging instrument and the second imaging instrument generates a second image. The tracking fixture is engageable along at least a portion of the second imaging instrument. The tracking fixture includes one or more features. The medical instrument is attachable to an attachment feature of the tracking fixture to maintain a known configuration of the medical instrument relative to (Continued)

the second imaging instrument. The processor is configured to determine a pose of the tracking fixture based on the one or more features of the tracking fixture and the first image.

20 Claims, 14 Drawing Sheets

(51) Int. Cl.
| | |
|---|---|
| *A61B 34/35* | (2016.01) |
| *A61B 90/96* | (2016.01) |
| *A61B 1/00* | (2006.01) |
| *A61B 10/04* | (2006.01) |
| *A61B 17/00* | (2006.01) |
| *A61B 17/29* | (2006.01) |
| *A61B 17/30* | (2006.01) |
| *A61B 18/00* | (2006.01) |
| *A61B 34/30* | (2016.01) |
| *A61B 90/00* | (2016.01) |

(52) U.S. Cl.
CPC .......... *A61B 90/96* (2016.02); *A61B 1/00193* (2013.01); *A61B 2010/045* (2013.01); *A61B 2017/00477* (2013.01); *A61B 2017/00876* (2013.01); *A61B 17/29* (2013.01); *A61B 2017/306* (2013.01); *A61B 2017/3413* (2013.01); *A61B 2018/00577* (2013.01); *A61B 2034/2055* (2016.02); *A61B 2034/2061* (2016.02); *A61B 2034/2063* (2016.02); *A61B 2034/2065* (2016.02); *A61B 2034/2072* (2016.02); *A61B 2034/302* (2016.02); *A61B 2090/364* (2016.02); *A61B 2090/3941* (2016.02); *A61B 2090/3945* (2016.02)

(58) Field of Classification Search
CPC .... A61B 2034/2055; A61B 2034/2061; A61B 2034/2063; A61B 2034/2072; A61B 2090/3941; A61B 2090/3945; A61B 90/96; A61B 2034/2065

See application file for complete search history.

(56) References Cited

U.S. PATENT DOCUMENTS

| | | | |
|---|---|---|---|
| 8,684,937 | B2 | 4/2014 | Sasady |
| 9,155,520 | B2 | 10/2015 | Schneider et al. |
| 2005/0267373 | A1 | 12/2005 | Lee |
| 2008/0030678 | A1 | 2/2008 | Razzaque et al. |
| 2009/0088897 | A1 | 4/2009 | Zhao et al. |
| 2010/0168562 | A1 | 7/2010 | Zhao et al. |
| 2011/0238043 | A1* | 9/2011 | Kleven .................. A61B 90/50 606/1 |
| 2012/0130415 | A1* | 5/2012 | Tal ................. A61B 17/320758 606/194 |
| 2013/0274598 | A1 | 10/2013 | Azizian et al. |
| 2014/0163736 | A1* | 6/2014 | Azizian .................. A61B 6/102 700/259 |
| 2014/0237828 | A1 | 8/2014 | Bucco |
| 2016/0081656 | A1* | 3/2016 | Abraham ............... A61B 8/582 600/439 |

OTHER PUBLICATIONS

International Search Report and Written Opinion for application No. PCT/US2017/066843. dated May 28, 2018, 13 pages.
Biopsy Needle Guides, Ultrasonix—Ultrasound your way, Jul. 2012, 7 pages.
International Preliminary Report on Patentability for Application No. PCT/US2017/066843, dated Jun. 27, 2019, 9 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

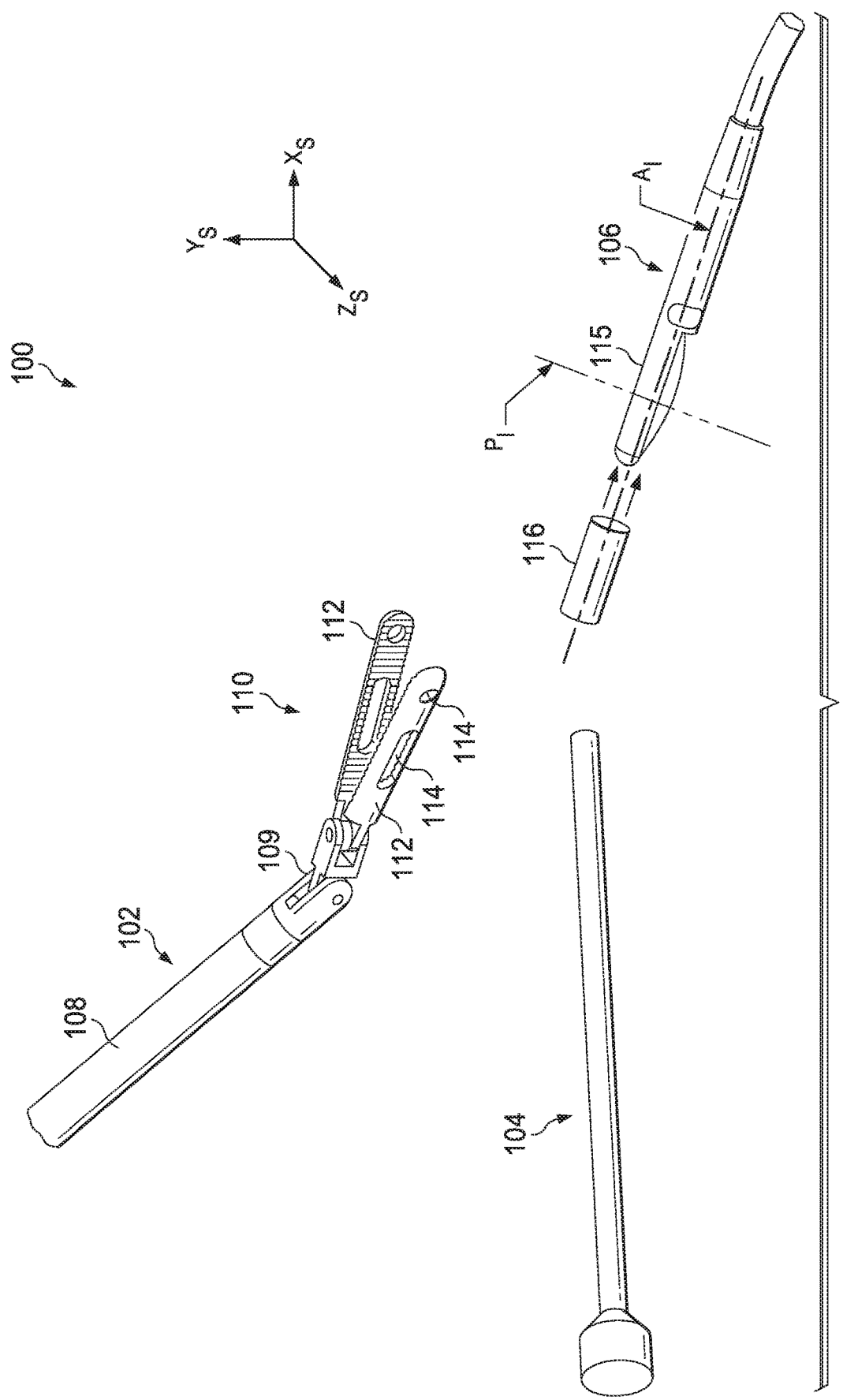

SYSTEMS AND METHODS FOR TELEOPERATED CONTROL OF AN IMAGING INSTRUMENT

RELATED APPLICATIONS

This patent application is the U.S. national phase of International Application No. PCT/US2017/066843, filed Dec. 15, 2017, which designated the U.S. and claims priority to and the benefit of the filing date of U.S. Provisional Patent Application 62/435,399, entitled "SYSTEMS AND METHODS FOR TELEOPERATED CONTROL OF AN IMAGING INSTRUMENT," filed Dec. 16, 2016, all of which are incorporated by reference herein in their entirety.

FIELD

The present disclosure is directed to systems and methods for using multiple imaging modalities in a minimally invasive surgical procedure and more particularly to systems and methods for coordinating images from the multiple imaging modalities.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic cameras. Some minimally invasive medical cameras may be teleoperated or otherwise computer-assisted. Endoscopic instruments allow a clinician to visualize the surgical environment inside the patient anatomy, but provide limited information about the anatomy beyond the surface of the visualized anatomic structures. Systems and methods are needed to provide additional imaging modalities within the surgical environment and to provide the information from the additional imaging modalities to the clinician in a coordinated presentation with the endoscopic information.

SUMMARY

The embodiments of the invention are summarized by the claims that follow below.

In one embodiment, a medical imaging system comprises a teleoperated assembly including a medical instrument. The medical imaging system also comprises a first imaging instrument for generating a first image of a field of view of the first imaging instrument and a second imaging instrument for generating a second image. A tracking fixture is engageable along at least a portion of the second imaging instrument. The medical instrument is attachable to the tracking fixture within the field of view of the first imaging instrument.

In another embodiment, a medical imaging system comprises a stereoscopic endoscopic instrument for generating a first image and a supplemental imaging instrument for generating a second image. The system also comprises a sleeve sized to extend along at least a portion of the supplemental imaging instrument. The sleeve is visible within an imaging area of the first image. The sleeve includes a marking scheme visible within the first image and upon which a pose of the sleeve relative to the stereoscopic endoscopic instrument is determined.

In another embodiment, a method comprises tracking movement of a medical instrument controlled by a teleoperated system and tracking a pose of an endoscopic instrument controlled by the teleoperated system. The method also comprises determining a pose of a supplemental imaging instrument with respect to a portion of the medical instrument. The supplemental imaging instrument is coupled to the medical instrument. The method also comprises determining a pose of the supplemental imaging instrument with respect to the endoscopic instrument based upon the determined pose of the supplemental imaging instrument with respect to the medical instrument.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 2 illustrates a set of minimally invasive tools for use in a minimally invasive surgical procedure.

DETAILED DESCRIPTION

Figure 1A:
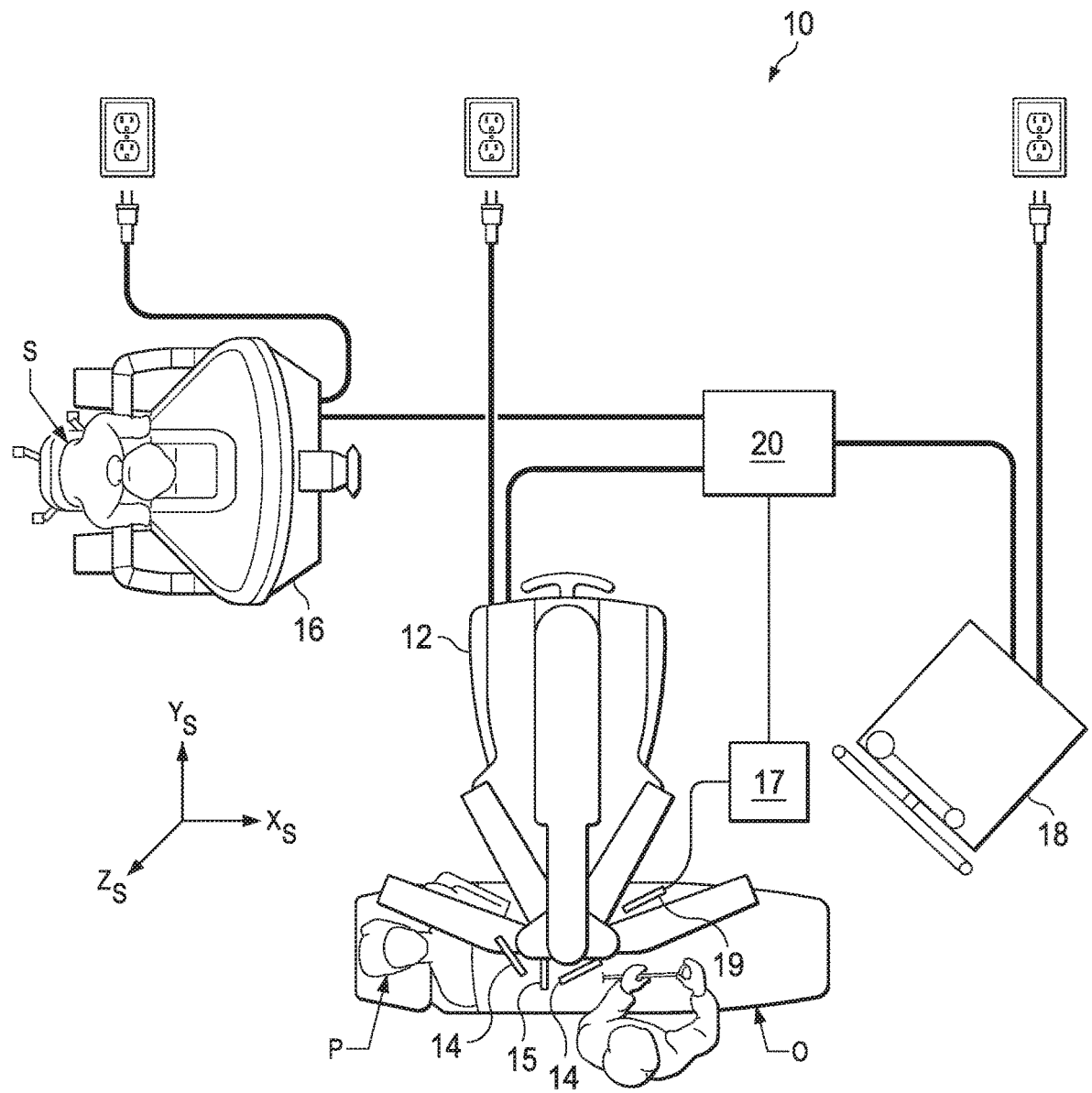
FIG. 1A is a schematic view of a teleoperated medical system in a surgical frame of reference, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1A of the drawings, a teleoperated medical system for use in, for example, medical procedures including diagnostic, therapeutic, or surgical procedures, is generally indicated by the reference numeral 10 and operates within a surgical environment having a surgical frame of reference coordinate system, $X_S$, $Y_S$, $Z_S$. As will be described, the teleoperated medical systems of this disclosure are under the teleoperated control of a surgeon. In alternative embodiments, a teleoperated medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperated medical system 10 generally includes a teleoperated assembly 12 mounted to or near an operating table O on which a patient P is positioned. The teleoperated assembly 12 may be referred to as a patient side cart. A medical instrument system 14 and an endoscopic imaging system 15 are operably coupled to the teleoperated assembly 12. An operator input system 16 allows a surgeon or other type of clinician S to view images of or representing the surgical site and to control the operation of the medical instrument system 14 and/or the endoscopic imaging system 15. A supplemental imaging system 17 including a minimally invasive image capture probe 19 may be used with the medical instrument system 14 and endoscopic imaging system 15 as will be described below. Together with the patient side cart, the supplemental imaging system 17 may be known as a patient side system. The endoscopic imaging system 15 provides images of the external surfaces of anatomic structures within the surgical environment. The supplemental imaging system 17 may be an internal imaging system such as an ultrasound, x-ray, or gamma imaging system capable of imaging beyond the external surface of the anatomical structures.

The operator input system 16 may be located at a surgeon's console, which is usually located in the same room as operating table O. It should be understood, however, that the surgeon S can be located in a different room or a completely different building from the patient P. The surgeon's console 16 includes left and right eye displays for presenting the surgeon S with a coordinated stereo view of the surgical site that enables depth perception. The console 16 further includes one or more input control devices which cause the teleoperated assembly 12 to manipulate one or more instruments or the endoscopic imaging system. The input control devices can provide the same degrees of freedom as their associated instruments 14 to provide the surgeon S with telepresence, or the perception that the input control devices are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperated assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperated assembly 12 supports and manipulates the medical instrument system 14 while the surgeon S views the surgical site through the console 16. An image of the surgical site can be obtained by the endoscopic imaging system 15, such as a stereoscopic endoscope, which can be manipulated by the teleoperated assembly 12 to orient the endoscope 15. An electronics cart 18 can be used to process the images of the surgical site for subsequent display to the surgeon S through the surgeon's console 16. The number of medical instrument systems 14 used at one time will generally depend on the diagnostic or surgical procedure and the space constraints within the operating room among other factors. The teleoperated assembly 12 may include a kinematic structure of one or more non-servo controlled links (e.g., one or more links that may be manually positioned and locked in place, generally referred to as a set-up structure) and a teleoperated manipulator. The teleoperated assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperated medical system 10 also includes a control system 20. The control system 20 includes at least one memory and at least one processor (not shown), and typically a plurality of processors, for effecting control between the medical instrument system 14, the endoscopic system 15, the operator input system 16, and monitors on the electronics system 18. The control system 20 may also receive and process images from the supplemental imaging system 17. The electronics cart 18 may house components of the endoscopic imaging system 15, the supplemental imaging system 17, the control system 20 as well as monitors and processors for processing and displaying captured images.

The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperated assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperated systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperated assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperated assembly 12. In some embodiments, the servo controller and teleoperated assembly are provided as part of a teleoperated arm cart positioned adjacent to the patient's body.

The teleoperated medical system 10 may further include optional operation and support systems (not shown) such as illumination systems, steering control systems, irrigation systems, and/or suction systems. In alternative embodiments, the teleoperated system may include more than one teleoperated assembly and/or more than one operator input system. The exact number of manipulator assemblies will depend on the surgical procedure and the space constraints within the operating room, among other factors. The operator input systems may be collocated, or they may be positioned in separate locations.

Figure 1B:
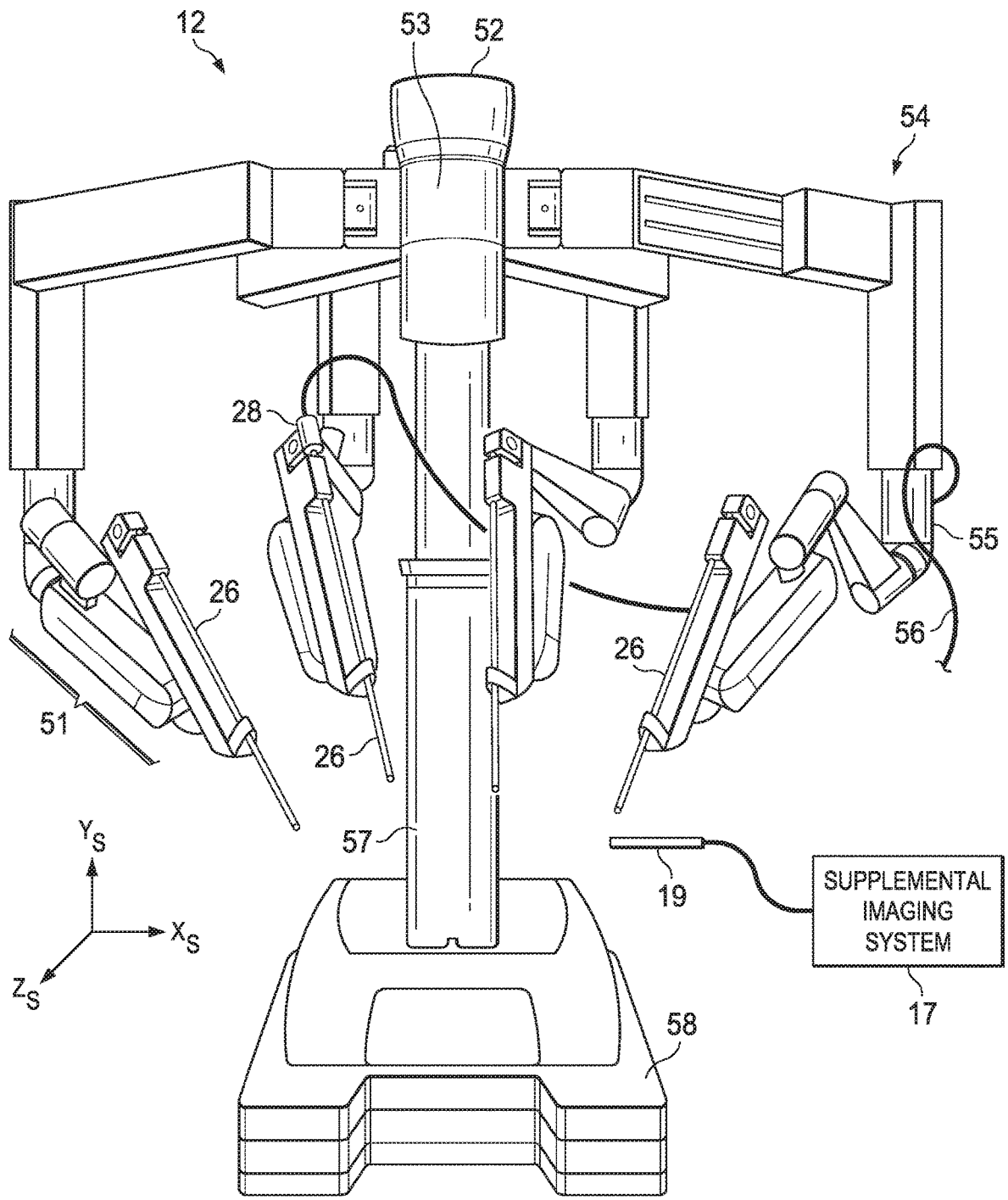
FIG. 1B is a perspective view of patient side systems, according to one example of principles described herein.

FIG. 1B is a perspective view of one embodiment of a teleoperated assembly 12 and a supplemental imaging system 17 which may, together, be referred to as a patient side system. The teleoperated assembly 12 shown provides for the manipulation of three surgical tools 26 (e.g., instrument systems 14) and an imaging device 28 (e.g., endoscopic imaging system 15), such as a stereoscopic endoscope used for the capture of images of the site of the procedure. The imaging device may transmit signals over a cable 56 to the electronics cart 18. Manipulation is provided by teleoperative mechanisms having a number of joints. The imaging device 28 and the surgical tools 26 can be positioned and manipulated through incisions or natural orifices in the patient so that a kinematic remote center is maintained at the incision to minimize the size of the incision. Images of the surgical site can include images of the distal ends of the surgical tools 26 when they are positioned within the field-of-view of the imaging device 28.

The patient side cart 12 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The patient side cart 12 may also include a telescoping horizontal cantilever 52 for moving the orienting platform 53 in a horizontal direction.

In the present example, each of the arms 54 connects to a manipulator arm 51. The manipulator arms 51 may connect directly to a surgical tools 26. The manipulator arms 51 may be teleoperable. In some examples, the arms 54 connecting to the orienting platform are not teleoperable. Rather, such arms 54 are positioned as desired before the surgeon begins operation with the teleoperative components.

The supplemental imaging system 17 may be an internal imaging system such as an ultrasound, optoacoustic, x-ray, gamma or radiofrequency (RF) imaging system capable of imaging beyond the external surface of the anatomical structures. The image capture probe 19 may be a minimally invasive imaging instrument sized for insertion into the surgical environment. The probe 19 may include a receiver arrangement, such as a gamma detector. The probe 19 may include a transmitter and receiver arrangement, such as an ultrasound transducer. The ultrasound transducer can be mounted at an end of an elongated shaft, an elongated cable or can be wireless. This imaging source can be used to obtain intraoperative two-dimensional or three-dimensional images, or model, of the anatomic environment. As a two-dimensional source, the ultrasonic transducer can be used to obtain a single ultrasound image. As a three-dimensional source it can be used to obtain a plurality of spaced ultrasonic images, or slices, thereby to provide sufficient information for construction of a three-dimensional model of a volume of interest. Accordingly, it can be arranged to move, including rotate, within an anatomic site to capture such images, or slices. This can typically be achieved, for example, in accordance with a pre-programmed sequence for moving the ultrasound transducer by teleoperated control, manual movement of the ultrasound transducer, or the like.

Endoscopic imaging systems (e.g., systems 15, 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image based endoscopes have a "chip on the tip" camera design in which a distal digital sensor such as a one or more charge-coupled device (CCD) or a complementary metal oxide semiconductor (CMOS) device acquire image data. Endoscopic imaging systems may provide two- or three-dimensional images of the endoscopic field of view (i.e. the imaging area) to the viewer. Two-dimensional images may provide limited depth perception. Three-dimensional stereo endoscopic images may provide the viewer with more accurate depth perception. Stereo endoscopic instruments employ stereo cameras to capture stereo images of the field of view of the patient anatomy. An endoscopic instrument may be a fully sterilizable assembly with the endoscope cable, handle and shaft all rigidly coupled and hermetically sealed.

Endoscopic imaging instruments allow the clinician to visualize the external surfaces of anatomic structures in the surgical environment but often are inadequate for visualizing sub-surface structures that may be the target of surgical procedures or that should be avoided during surgical procedures. Such sub-surface structures may include tumors, cysts, bony anatomy, blood vessels, ureters, bile ducts, nerves, lymph nodes, or the like. Other imaging modalities, such as ultrasound, provide visualization of these sub-surface structures. Although this disclosure will generally refer to ultrasound technology as the supplemental imaging technology, other sub-surface imaging modalities may also be used. Ultrasound is a suitable imaging modality for sub-surface visualization because it provides reasonable soft tissue contrast. It can be used intra-operatively and provides real-time images. Ultrasound uses mechanical vibration and thus is relatively harmless to the patient. Ultrasound technology is also cost-effective and widely available. Ultrasound has found limited application in minimally invasive surgery because of a lack of hand-eye coordination between the surgical instruments under the control of the clinician and the endoscopic and ultrasound images. Additionally, interpretation of the ultrasound images as cut-through slices with respect to the anatomy of interest has been difficult with unstable transducer positions. Using the systems and methods described below, coordination between the ultrasound images, the endoscopic images, and the surgical instruments under the clinician's control may be improved.

To improve the coordination of the ultrasound images visible to the clinician with the clinician's endoscopic view of the surgical environment and the control of the medical instruments in the surgical environment, the pose of the ultrasound probe with respect to the endoscopic instrument is determined. The pose of the ultrasound probe with respect to the endoscope may be determined directly by endoscopic images of the ultrasound probe, as will be described below. Alternatively, the pose of the ultrasound probe with respect to the endoscope may be determined indirectly by first determining the pose of the probe with respect to the teleoperated medical instrument holding and moving the probe. Then, the pose of the medical instrument holding the ultrasound probe may be determined by instrument tracking in the surgical coordinate space. The pose of the endoscopic instrument may also be determined by instrument tracking in the surgical coordinate space. The determined pose of the ultrasound probe with respect to the medical instrument may be transformed into the surgical coordinate space. Because the ultrasound probe pose and the endoscope pose are both known in the surgical coordinate space, the pose of the ultrasound probe with respect to the endoscopic instrument may be determined. Instrument tracking of the medical instrument and the endoscopic instrument may be achieved by reading joint encoders or other sensors in the teleoperated assembly 12 and applying a kinematic model of the teleoperated arms and the instruments to determine the position and orientation of the distal tips of the medical and endoscopic instruments.

FIG. 2 illustrates distal ends of a set of minimally invasive tools for use in a minimally invasive surgical procedure in a surgical environment 100 within the patient anatomy and the surgical reference frame $X_S$, $Y_S$, $Z_S$. The tools include a medical instrument 102 (e.g., from an instrument system 14), a stereoscopic endoscopic imaging instrument 104 (e.g., from the imaging system 15), and supplemental imaging instrument 106 (e.g., from the supplemental imaging system 17). The medical instrument 102 includes an elongated shaft 108 coupled by a wrist 109 to an end effector 110. The end effector 110 may be a forceps or other gripping mechanism including pivotally coupled gripping arms 112. The gripping arms 112 may include gripping features 114 including openings, channels, recessed areas, projections, or other structures or voids that may facilitate gripping material between the arms 112. The endoscope imaging instrument 104 transmits two or three-dimensional images of the surgical environment to the displays visible to the clinician. In this embodiment, the supplemental imaging instrument 106 is an ultrasound probe. The ultrasound probe may be a side-imaging probe including a rotating ultrasound transducer for imaging in a direction generally perpendicular to the axis of rotation of the transducer. The side-imaging probe generates a cross-sectional (i.e., radial) image along an imaging plane $P_I$ with an axis $A_I$ of rotation of the transducer. In other embodiments, a forward-looking ultrasound probe may be used to image tissue distal of the imaging transducer. The ultrasound probe may be relatively small to navigate narrow anatomical passageways. For example, the ultrasound probe may have distal end diameter of approximately 1.4 mm. The elongated distal portion 115 of the supplemental imaging instrument 106 houses the transducer. The instrument 102, the endoscope 104, and the probe 106 may enter the patient's body through one or more natural orifices or surgically created openings and may extend into the surgical environment 100 within the patient anatomy.

As described above, ultrasound images from the probe 106 may be transformed and coordinated with the endoscopic images of the field of view of the endoscope 104 to provide the clinician with an accurate understanding of the location of the structures visible in the ultrasound images, relative to the instruments under the clinician's control. In some embodiments, the pose of the ultrasound probe with respect to the endoscope may be determined directly by endoscopic images of the field of view that include the ultrasound probe. The probe 106 may be driven manually or may be driven by attachment to the teleoperated medical instrument 102. One way to directly track the movement of probe 106 is through the use of markings on the probe that can be visualized with the stereoscopic endoscope to determine the three dimensional pose of the probe. The markings may be directly applied to the probe. Alternatively, the markings may be incorporated in to a tracking fixture 116 that is removably attached to the probe 106. As shown in FIG. 2, the tracking fixture 116 is sized to attach to the distal portion 115 of the ultrasound probe 106. The tracking fixture 116 may slide on, clip to, or otherwise attach to the distal portion 115 so that the tracking fixture is fixed with respect to the distal portion 115 while the probe 106 is in operation and capturing ultrasonic images. The tracking fixture 116 may be configured as an elongated sleeve, an open channel, a closed-end sock, or other shape that extends at least partially along the length of the distal portion 115 of the probe 106. In some embodiments, the tracking fixture may be a non-removable component of the probe.

Figure 3A:
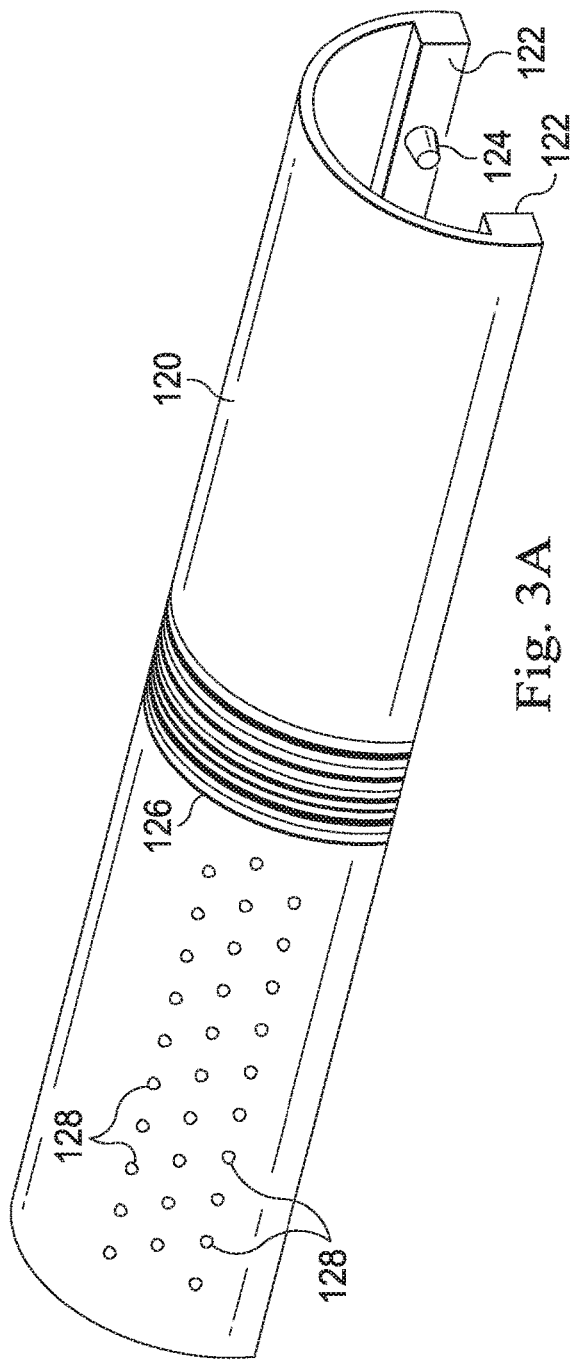
FIG. 3A illustrates a tracking fixture for use in tracking movement of an imaging device.
Figure 3B:
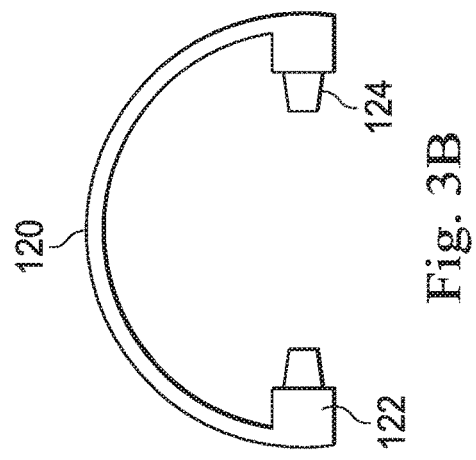
FIG. 3B illustrates an end view of the tracking fixture of FIG. 3A.
Figure 4A:
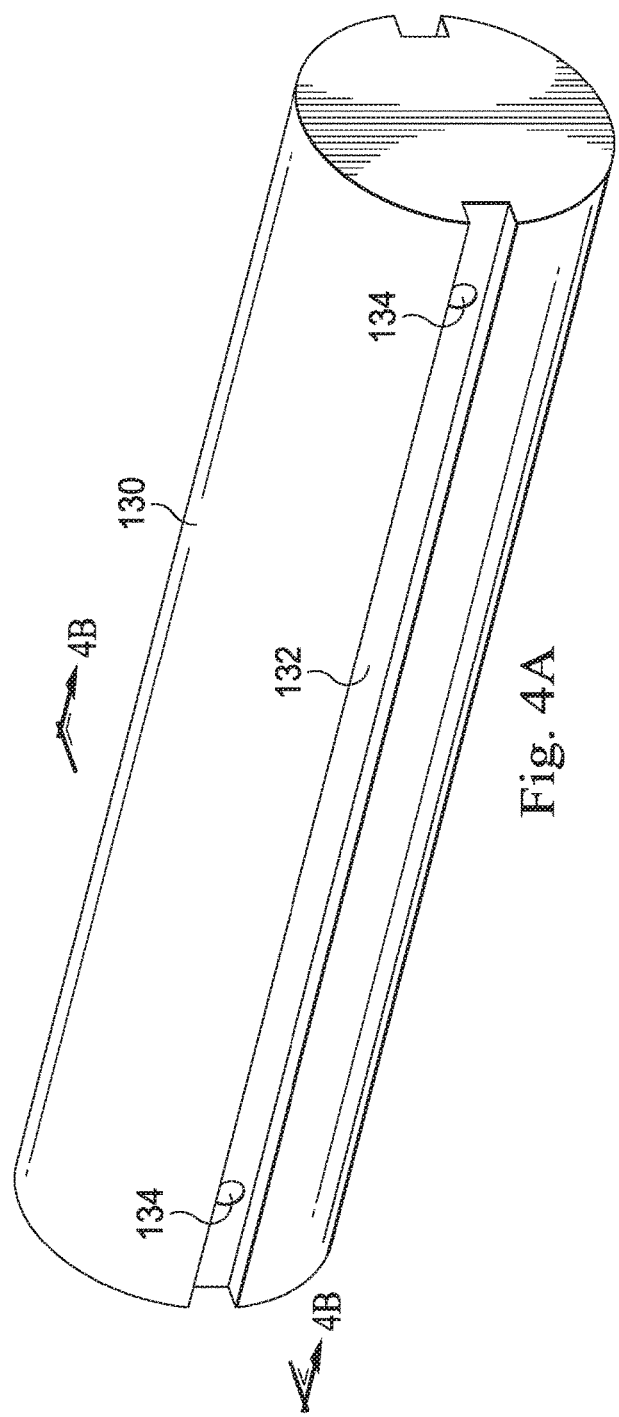
FIG. 4A illustrates a distal end of an imaging instrument according to an embodiment of this disclosure.
Figure 4B:
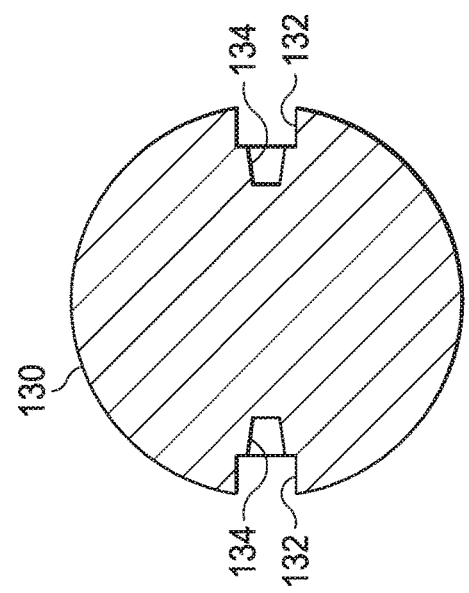
FIG. 4B illustrates an end view of the imaging instrument of FIG. 4A.

FIGS. 3A and 3B illustrate one example of a tracking fixture 120. Tracking fixture 120 has an elongated channel-shaped sleeve body with an engagement feature such as a pair of rails 122 extending inwardly toward the open channel. FIGS. 4A and 4B illustrate one example of a probe 130 (e.g, the probe 106) configured to mate with the tracking fixture 120. The probe 130 includes a pair of elongated grooves 132 sized to receive the rails 122. The grooves 132 may be parallel. The fixture 120 may slide on to or snap to probe 130. The fixture 120 may be mounted to the probe 130 to prevent sliding, rotation or other movement of the fixture relative to the probe. The fixture 120 may be configured to mount in a single position relative to the probe 130. For example, the tracking fixture 120 may have one or more pins 124 extending from the rails 122 or the inside of the channel. The pins 124 may be non-symmetric in that a pin extending from the right rail may be located at a different distance from the end of the fixture than a pin extending from the left rail. The pins 124 are sized to mate or snap in only one way to indentions 134 in the elongated grooves 132. The indentions 134 for each groove are located at non-symmetric distances. Other engagement features may be used to limit the coupling of the tracking fixture to the probe in a single configuration.

The fixture 120 includes a plurality of markers that form a two-dimensional or three-dimensional pattern on the tracking fixture. The markers are located on an external surface and are visible with the stereoscopic endoscope. As one example, markers 126 provide a barcode pattern. In other alternative or additional embodiments, markers may form a monochromatic or colored pattern (e.g., a chessboard pattern). Optionally, the markers may include fluorescent material detectable by the stereoscopic endoscope and/or by a fluorescent imaging system associated with the endoscope system. As another example, markers 128 may comprise active components such as light emitting devices (LEDs). The active components may be powered and controlled through a connection with a medical instrument holding the tracking fixture or through a connection with the probe 130.

Figure 5:
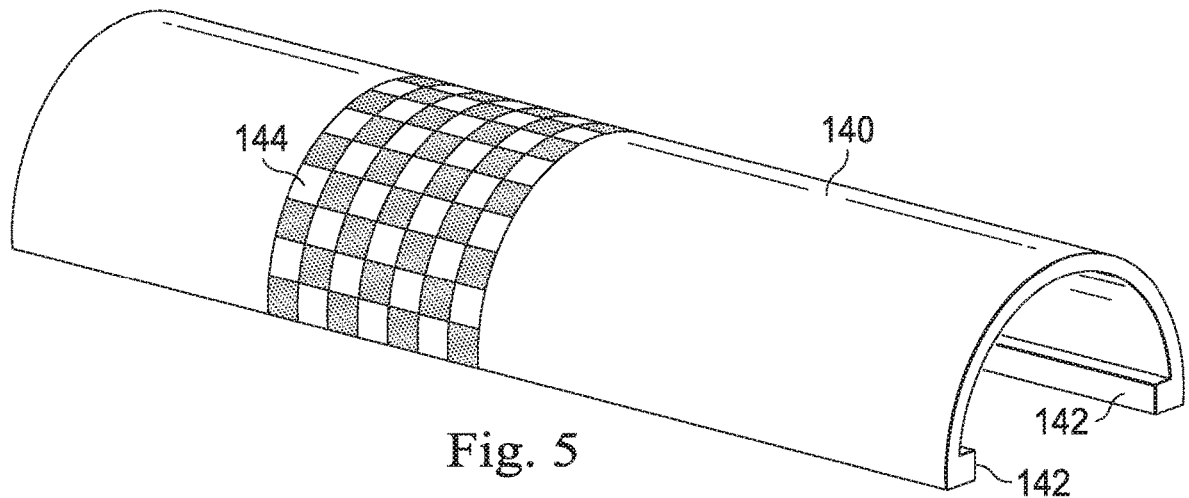
FIG. 5 illustrates a tracking fixture for use in tracking movement of an imaging device according to another embodiment of this disclosure.

FIG. 5 illustrates another example of a tracking fixture 140. Tracking fixture 140 has an elongated generally cylindrical sleeve body with a pair of rails 142 extending inwardly toward the elongated opening of the cylindrical body. In this embodiment, a marker 144 has a checkerboard pattern that may be tracked by the endoscopic instrument.

The markers on the tracking fixture are rigidly arranged in predetermined patterns and are visible in the acquired endoscopic images. Because the true relative position of the marker pattern in the surgical environment is known, the control system 20 is able to calculate from the stereo-endoscopic images, the distance of the marker pattern from the endoscopic instrument and, consequently, the pose of the tracking fixture relative to the endoscopic instrument. The markers may be three dimensional or may be constructed using thin films or inks that are essentially two-dimensional in nature. Many possible shapes, such as, by way of non-limiting example, circles, squares, triangles, rectangles, ovals, and alphanumeric or other symbols, can be used to design the markers. Various types of fiducial marker design are described in U.S. patent application Ser. No. 12/428,657, entitled "Fiducial Marker Design and Detection for Locating Surgical Instrument in Images," filed Apr. 23, 2009, which is incorporated by reference herein in its entirety.

In any of the embodiments described, the tracking fixture may be disposable after a single or limited number of uses. Different tracking fixtures may be used for different procedure types. In some embodiments, for example, the tracking device may include a balloon, membrane or other expandable member that can be inflated with a fluid to provide access for ultrasound imaging when the probe surface cannot be placed into full contact with the anatomy of hard-to-reach areas.

Figure 6:
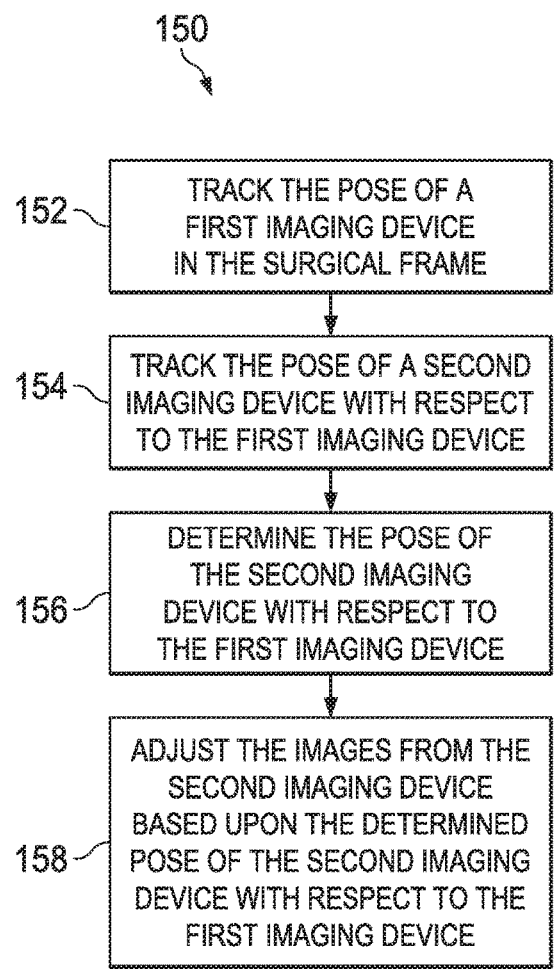
FIG. 6 is a flowchart illustrating a method for coordinating images from multiple imaging modalities during a minimally invasive surgical procedure.

FIG. 6 is a flowchart illustrating a method 150 for coordinating images from multiple imaging modalities during a minimally invasive surgical procedure. At a process 152, the pose of a distal end of a stereoscopic endoscopic instrument (e.g., instrument 104) may be tracked in the surgical environment coordinate space. The endoscope may be tracked by reading joint encoders or other sensors in the teleoperated assembly 12 and applying a kinematic model of the teleoperated arms and the instruments to determine the position and orientation of the distal tip of the endoscopic instrument. At a process 154, the pose of a supplemental imaging device (e.g., the ultrasound probe 106) is tracked with respect to the endoscopic instrument. In one embodiment, as described above, the supplemental imaging device may be tracked using a tracking fixture (e.g., 116, 120, 130, 140) attached to the distal end of the supplemental imaging device from which supplemental images are acquired. At a process 156, the pose of the supplemental imaging device with respect to the endoscopic device is determined. For example the pose of the ultrasound probe with a tracking fixture may be determined with respect to the endoscopic device by calculating the distance of the markers on the tracking fixture to the distal end of the endoscopic device. Optionally, the pose of the supplemental imaging device may be transformed from the endoscopic device frame of reference to the surgical environment frame of reference.

At a process 158, images obtained from the supplemental imaging device are modified based upon the determined pose of the supplemental imaging device with respect to the endoscopic instrument. For example, a three-dimensional warped ultrasound image may be displayed in corrected three-dimensional alignment as an overlay on the stereo endoscopic image. Alternatively, a three-dimensional warped ultrasound image may be displayed as a picture-in-picture with corrected alignment along with the stereo endoscopic image. Alternatively, images of virtual instruments corresponding to tracked medical instruments in the surgical environment may be displayed as a three dimensional overlay on the ultrasound image. Alternatively, a plurality of two-dimensional ultrasound images may be used to display three-dimensional reconstructions. For example, volumetric reconstructions may be made with two dimensional B-mode images. As another example, Doppler ultrasound images may be used to generate three-dimensional centerline or mesh reconstructions of blood vessels.

Figure 7:
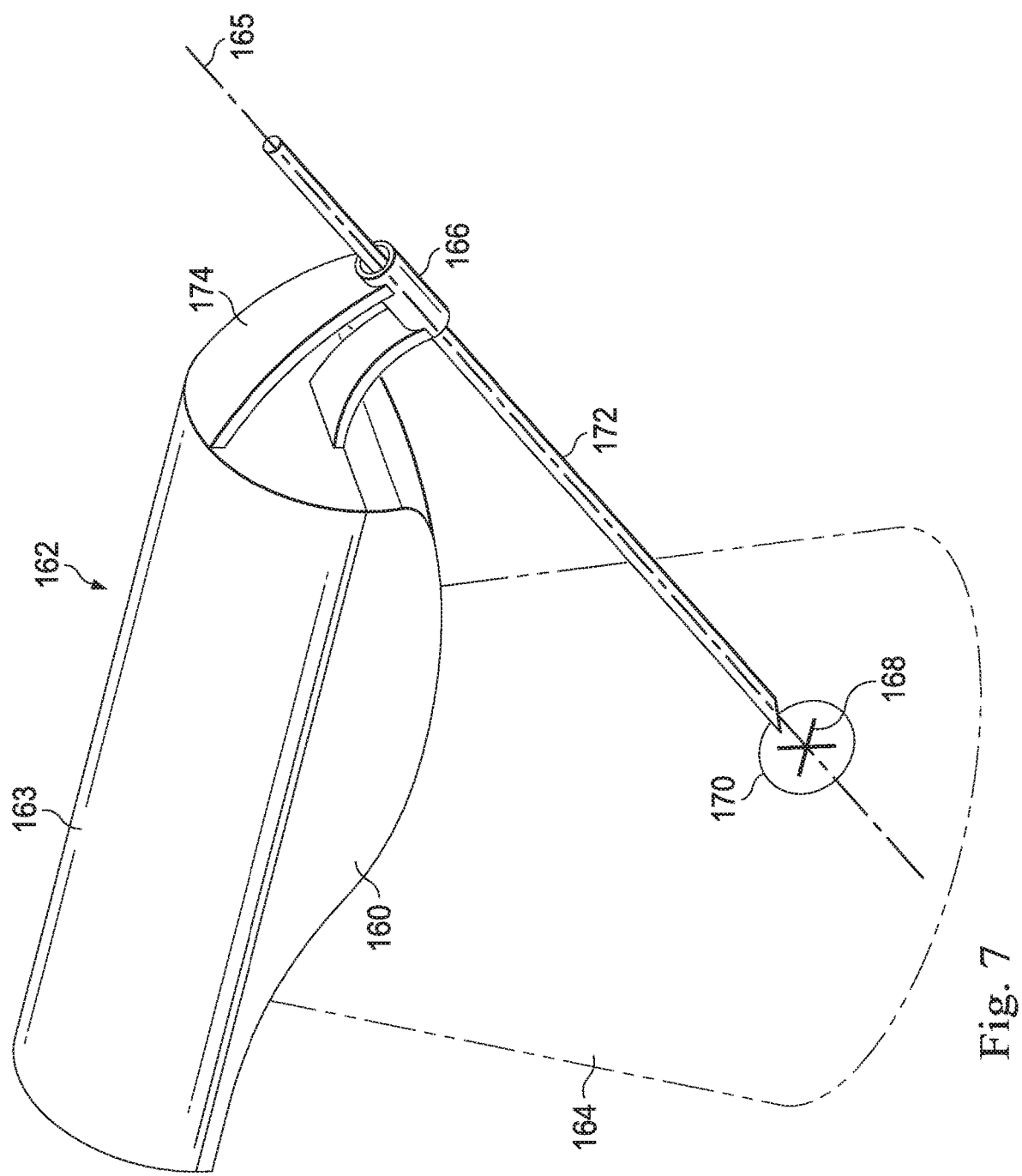
FIG. 7 illustrates a distal end of an imaging instrument with a tracking fixture according to an embodiment of this disclosure.

FIG. 7 illustrates a distal end of an imaging probe 160 with a tracking fixture 162. The imaging probe obtains images from an image plane 164. In this embodiment the tracking fixture 162 includes an elongated sleeve 163, similar to the fixture 120, and further including a guide member 174 extending from a distal end of the tracking fixture and distally of the imaging probe 160. The guide member 174 includes a guide channel 166. The guide channel 166 is fixed in a known and rigid configuration relative to the sleeve 163 and thus is fixed in a rigid configuration relative to the probe 160 when the tracking fixture is coupled to the probe. A trajectory 165 through the guide channel intersects the image plane 164. The intersection point 168 or line along 172 may be shown on the ultrasound image visible to the clinician to facilitate targeting of a lesion 170. The guide channel 166 is sized to receive a medical instrument 172 such as a needle, biopsy forceps, ablation needle, or other tool for assessing or treating a target location in the patient anatomy. The medical instrument 172 may be directed by manual or teleoperated control. A needle extended through the guide channel 166 may be used to inject material into a target lesion or surrounding area. The material may be a contrast agent injected peripherally to a lesion to study drainage patterns in lymph nodes surrounding the lesion. Alternatively, the injected material may be a therapeutic agent or pharmaceutical treatment. Because the clinician has a spatial understanding of the relationship between the instrument trajectory and the probe 160, the instrument 172 may be used to perform precision procedures including the ablation of tissue and tissue biopsies. The instrument 172 may also be used to deposit fiducial markers to mark the location of a lesion. The markers may include a radiopaque material for detection by an x-ray imaging device. Additionally or alternatively, the markers may include radioisotopes for imaging with a gamma camera. The instrument 172 may also be used to carry a microscopic imaging probe such as a confocal microscopy probe or an optical coherence tomography (OCT) probe.

Figure 8A:
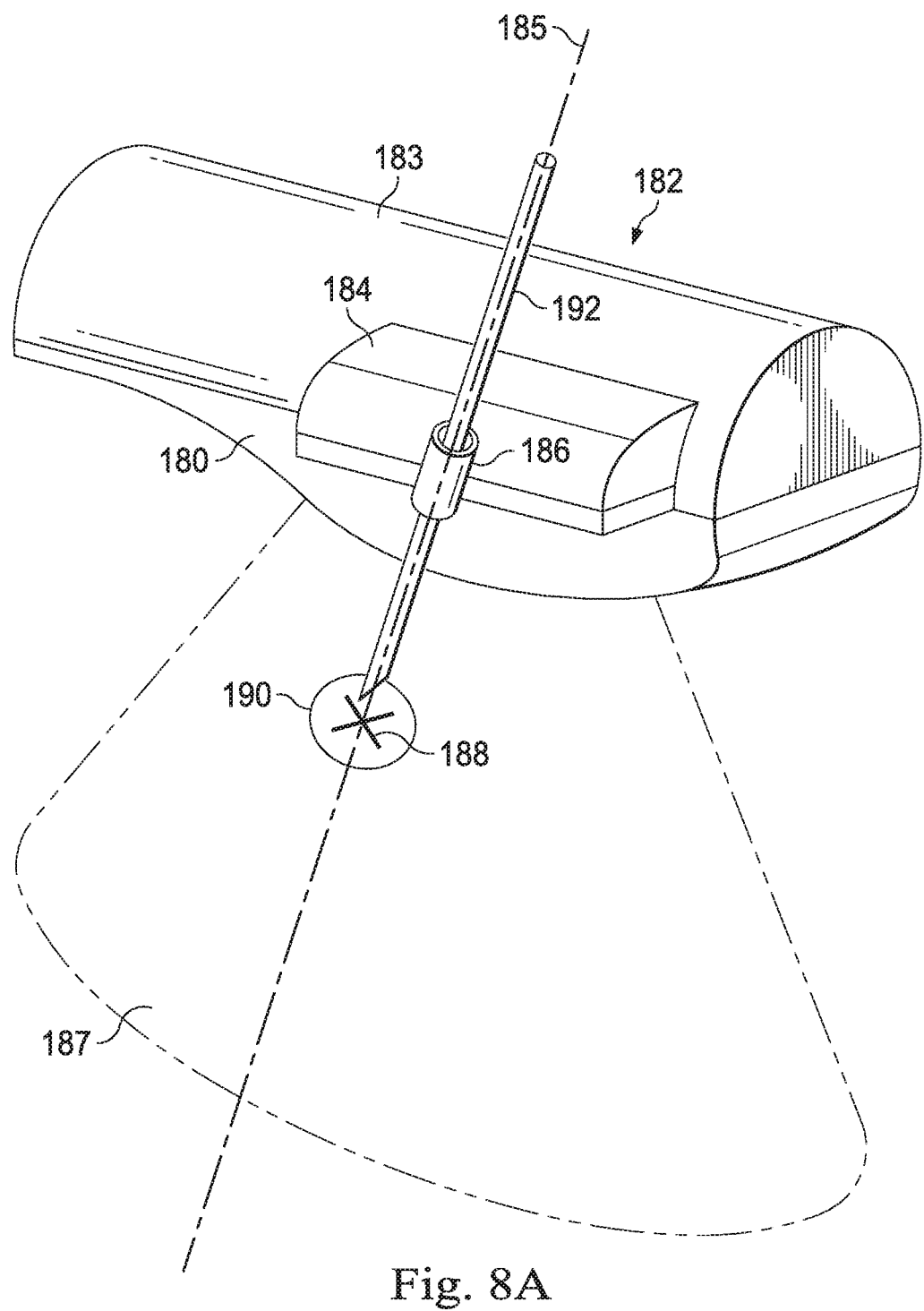
FIG. 8A illustrates a distal end of an imaging instrument with a tracking fixture according to another embodiment of this disclosure.
Figure 8B:
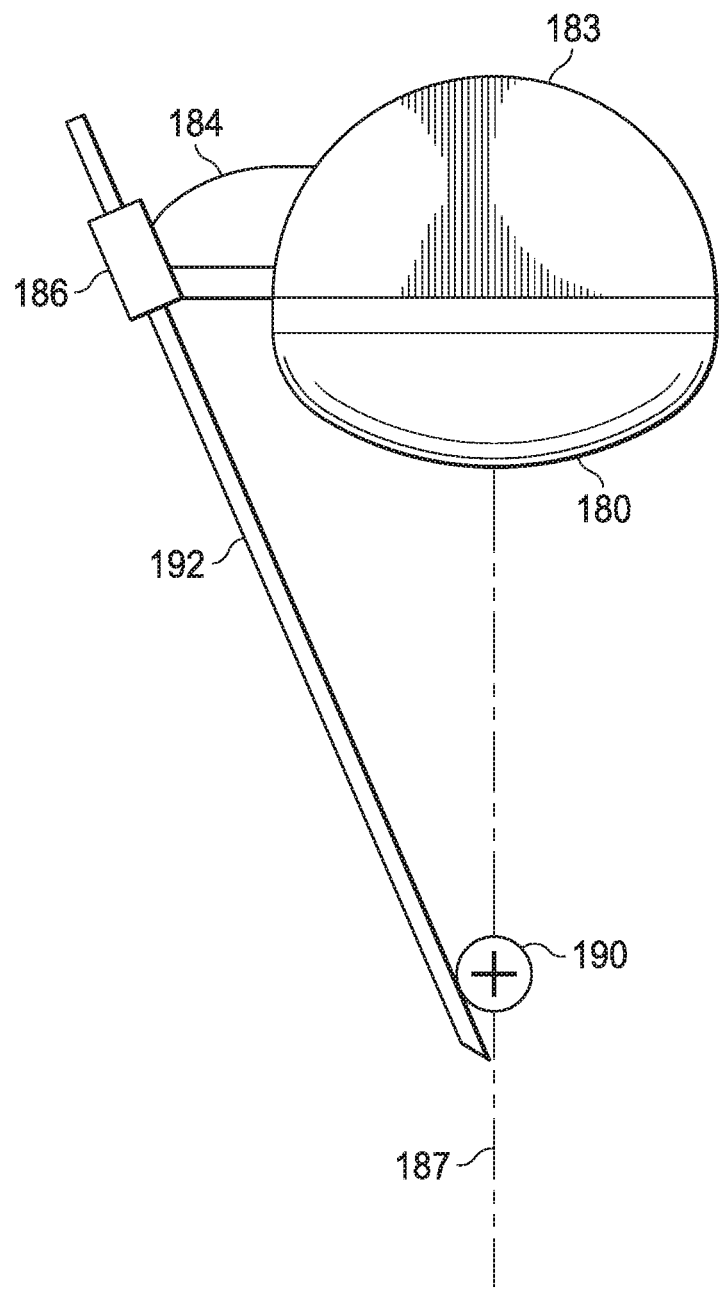
FIG. 8B illustrates an end view of the imaging instrument and tracking fixture of FIG. 8A.

FIGS. 8A and 8B illustrate a distal end of an imaging probe 180 with a tracking fixture 182. The imaging probe obtains images from an image plane 187. In this embodiment the tracking fixture 182 includes an elongated sleeve 183 similar to the fixture 120 and further including a guide member 184 extending laterally from a side of the tracking fixture and laterally of the imaging probe 180. The guide member 184 includes a guide channel 186. The guide channel 186 is fixed in a known and rigid configuration relative to the sleeve 183 and thus is fixed in a rigid configuration relative to the probe 180. A trajectory 185 through the guide channel intersects the image plane 187. The intersection point 188 may be shown on the ultrasound image visible to the clinician to facilitate targeting of a lesion 190. The guide channel 186 is sized to receive a medical instrument 192 such as a needle, biopsy forceps, ablation needle, or other tool for assessing or treating a target location in the patient anatomy. Because the clinician has a spatial understanding of the relationship between the instrument trajectory and the probe 180, the instrument 192 may be used to perform precision procedures as described above.

Figure 8C:
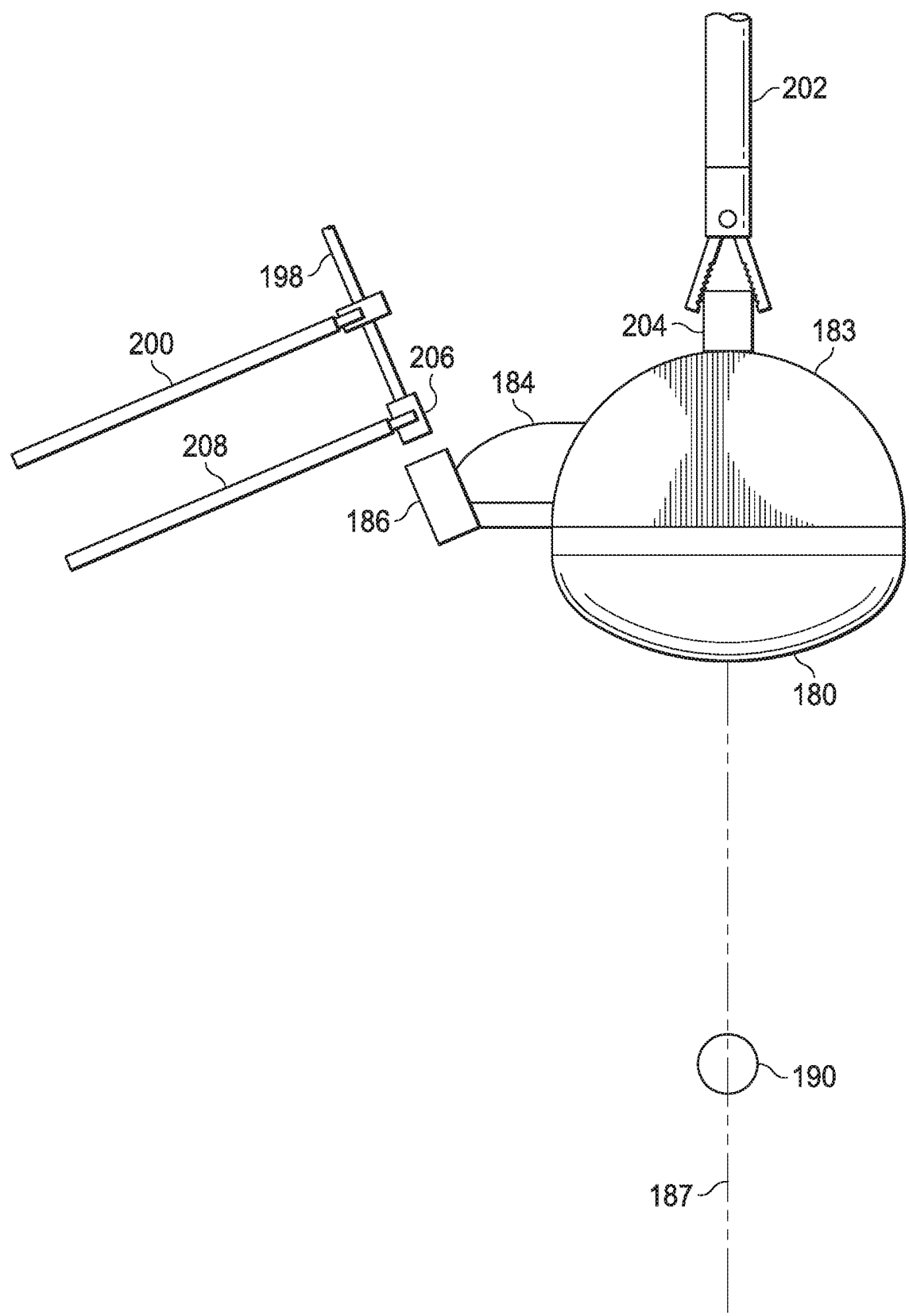
FIG. 8C illustrates a tracking fixture according to another embodiment of this disclosure.

In FIG. 8C, a teleoperated medical instrument 202 grips a projection 204 extending from the sleeve 183. A medical instrument 198 may be, for example, an elongated butterfly needle or a coaxial needle-sheath system. The medical instrument 198 is held and moved under the control of a medical instrument 200. The instrument 198 is inserted through the guide channel 186 as the clinician confirms alignment of the needle and channel in endoscopic images. The endoscopic images provide visual cues about the trajectory needed to align the instrument 198 with the guide channel 186. The instrument 198 may be tracked in stereo endoscopic images and the control system of the teleoperated system may use the data from the endoscopic images to calculate a desired pose for the manipulator arm controlling the instrument 200 to bring the instrument 198 into alignment with the guide channel 186. In one alternative, the teleoperated system may command the manipulator arms to move to the desired pose. In another alternative, the teleoperated system may provide visual cues or haptic guides to the clinician controlling the operator inputs to guide the clinician in moving the operator inputs to create alignment of the instrument 198 with the guide channel 186.

In another alternative, the instrument 198 may be inserted percutaneously by manual advancement of the instrument 198 through a needle guide 206 positioned externally of the patient anatomy. The external needle guide 206 may be held by a teleoperated medical instrument 208. The teleoperated medical instrument 208 aligns a trajectory of the needle guide 208 with the guide channel 186 based on the data received from the endoscopic images. Alternatively, instead of or in addition to using the teleoperated needle guide 206, a laser marker may be used to indicate the desired percutaneous insertion point so that a line passing through the marked point and a centroid of the guide channel 186 aligns with the direction of the guide channel.

As described above, ultrasound images from the probe 106 may be transformed and coordinated with the endoscopic images from the endoscope 104 to provide the clinician with an accurate understanding of the location of the structures visible in the ultrasound, relative to the instruments under the clinician's control. In some embodiments, the pose of the ultrasound probe with respect to the endoscope may be determined indirectly by the probe's known or determined relationship with respect to the teleoperated medical instrument holding the probe. The pose of the medical instrument holding the ultrasound probe may be determined by instrument tracking in the surgical coordinate space.

In one embodiment, a tracking fixture of an imaging probe, as described above, may include a connector that couples to the teleoperated medical instrument 102 in a single, predefined configuration so that the pose of the probe 106 relative to the instrument 102 remains unchanged throughout the procedure. The pose of the probe 106 relative to the endoscope is determined from the known relationship between the medical instrument 102 and the probe and the fixed relationship between the medical instrument and the probe. However, such a connector may limit the range of movement and therefore the use of the imaging probe. In another embodiment, the ultrasound transducer may be integrated into the teleoperated medical instrument 102. This embodiment may be limited by cost, sterilization requirements, and lifecycle constraints.

Figure 9:
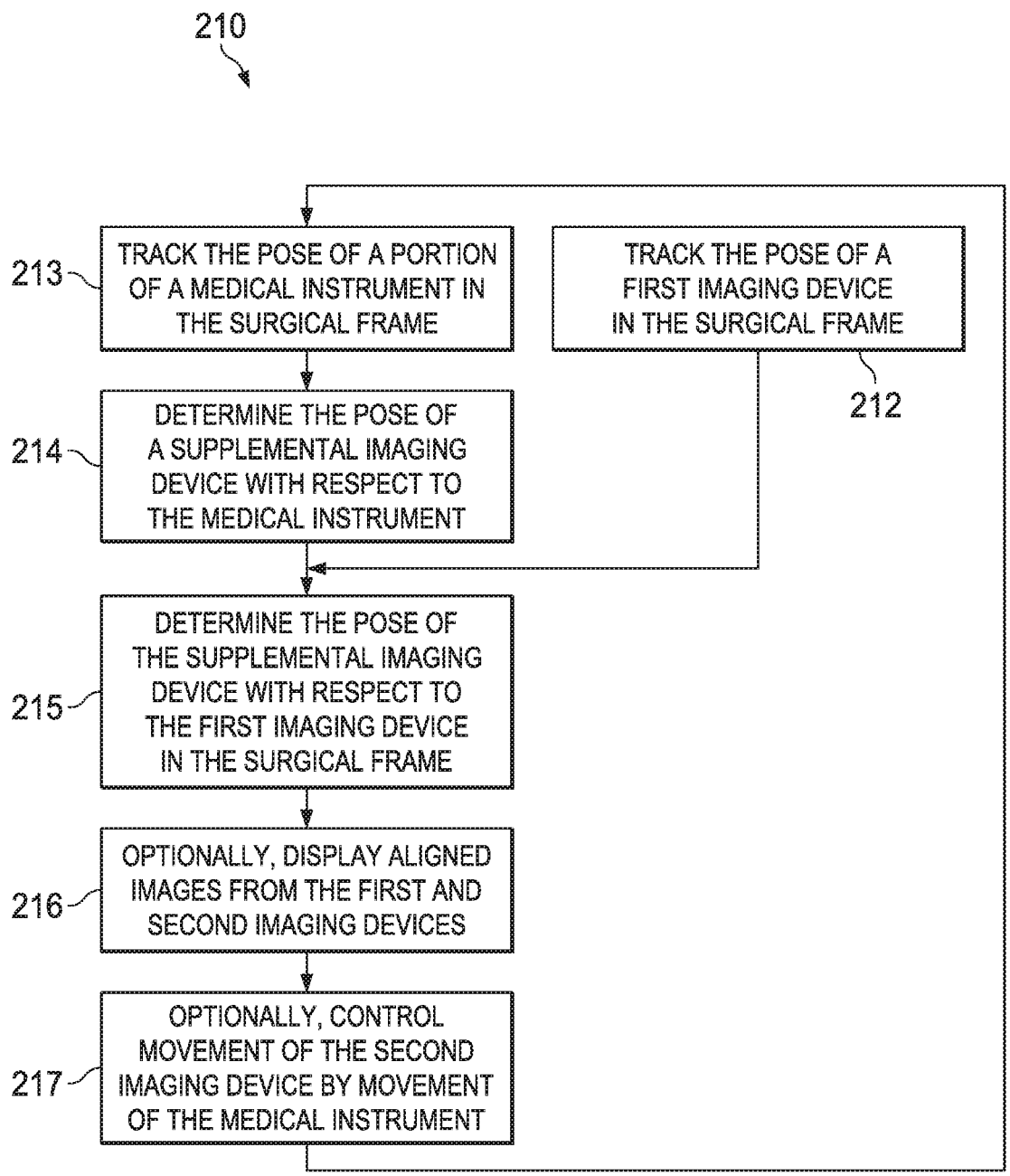
FIG. 9 is a flowchart illustrating a method for coordinating images from multiple imaging modalities during a minimally invasive surgical procedure.

In various embodiments, as described in examples below, the imaging probe may have a variable relationship to the holding medical instrument; however, the relationship between the probe and the tracked holding instrument may be determined or tracked so that ultimately the pose between the imaging probe and the endoscopic instrument may be determined. FIG. 9 is a flowchart illustrating a method for coordinating images from multiple imaging modalities during a minimally invasive surgical procedure based on tracking a medical instrument holding one of the imaging devices. At a process 212, the pose of the endoscope (e.g., endoscope 104) in the surgical reference frame may be determined, for example, from the kinematic model of the endoscope coupled to the teleoperated system. At a process 213, the pose of a portion of a medical instrument (e.g., instrument 102) in the surgical frame may be tracked. For example, the distal end of the medical instrument may be determined from the kinematic model of the medical instrument coupled to the teleoperated system or from the use of an optical fiber shape sensor extended within the instrument and having a shape measurable with respect to a known fixture or component such as the teleoperated assembly 12 in the surgical frame. The medical instrument may be coupled to a supplemental imaging device (e.g., the ultrasound probe 106) to hold the probe and guide the probe within the surgical environment. At a process 214, a pose of the probe with respect to the medical instrument (e.g., the distal end of the medical instrument) holding the probe may be determined. In various embodiments described below, the pose of the probe may be determined relative to the medical instrument by using a tracking mechanism fixed to the probe. The medical instrument may be coupled to the tracking mechanism in various known or determinable configurations so that the pose of the medical instrument relative to the probe can ultimately be determined. At a process 215, the pose of the probe device with respect to the endoscope is obtained by combining the determined pose of the distal end of the medical instrument and the determined pose of the probe with respect to the distal end of the medical instrument or by directly determining the pose of the probe with respect to the first imaging device. Optionally, at a process 216, aligned images from the endoscope and the probe may be displayed to the clinician. The images obtained from the probe are modified based upon the determined pose of the probe with respect to the endoscopic instrument. For example, a three-dimensional warped ultrasound image may be displayed in corrected three-dimensional alignment as an overlay on the stereo endoscopic image. Alternatively, a three-dimensional warped ultrasound image may be displayed as a picture-in-picture with corrected alignment along with the stereo endoscopic image. Alternatively, images of virtual instruments corresponding to tracked medical instruments in the surgical environment may be displayed as a three dimensional overlay on the ultrasound image. Alternatively, a plurality of two-dimensional ultrasound images may be used to display three-dimensional reconstructions. For example, volumetric reconstructions may be made with two dimensional B-mode images. As another example, Doppler ultrasound images may be used to generate three-dimensional centerline or mesh reconstructions of blood vessels.

After viewing the aligned ultrasound and endoscopic images, the clinician may direct movement of the probe to obtain additional images from a different pose of the probe. At a process 217, the probe may be directed to a different location or different pose by movement of the medical instrument holding the probe. The determination of the pose of the probe relative to the endoscope may be repeated for each movement of the probe.

Figure 10:
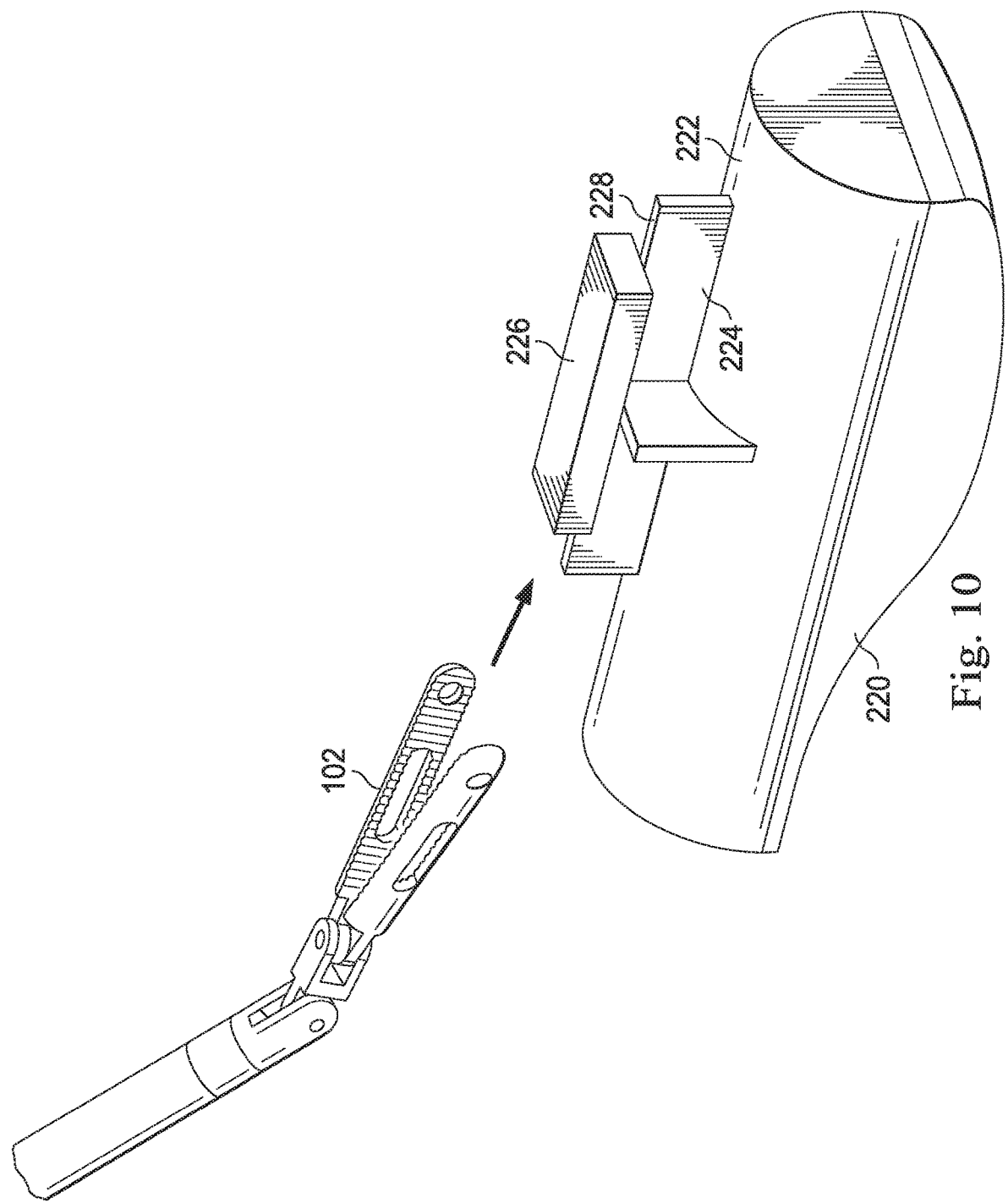
FIG. 10 illustrates a distal end of an imaging instrument with a tracking fixture according to another embodiment of this disclosure.

In various embodiments, the pose of the medical instrument relative to the probe may be adjustable or variable. As shown in FIG. 10, a distal end of an imaging probe 220 is fitted with a tracking fixture 222 which may include some or all of the features previously described for tracking fixtures. In this embodiment, the tracking fixture 222 includes a coupling mechanism 224. The coupling mechanism 224 includes a channel 226 sized to receive an end effector of the teleoperated medical instrument 102. A flexible connector 228 couples the channel 226 to the elongated body of the tracking fixture 222. In this embodiment, the flexible connector may be made of rubber or another type of elastic material that provides limited movement of the coupled end effector relative to the tracking fixture. Because the pose of the instrument 102 end effector is known in the surgical space and because the end effector has limited movement when coupled to the tracking fixture 222, the pose of the probe 220 can be approximately determined from the pose of the instrument 102 end effector. Further estimation of the pose of the probe 220 is done by tracking the tracking fixture 222, directly or via the probe location, in the endoscopic images. In various embodiments, the pose of the probe 220 may be determined by a shape sensor extending within a cable coupled to the probe. The shape sensor may provide the pose of the probe with respect to the teleoperated assembly 12 or other known location within the surgical frame of reference.

Figure 11:
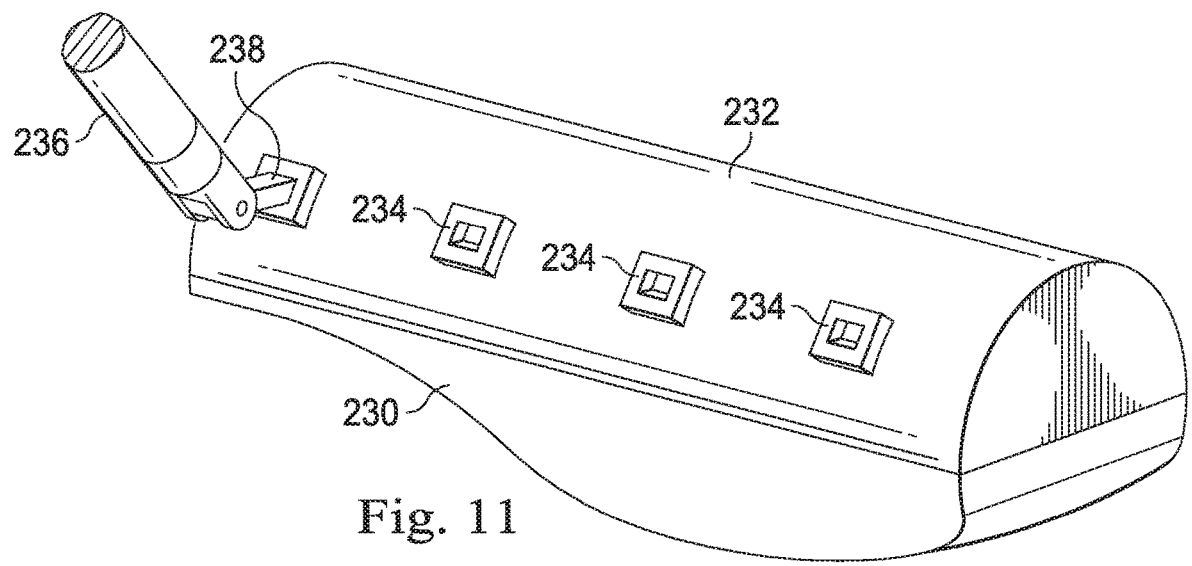
FIG. 11 illustrates a distal end of an imaging instrument with a tracking fixture according to another embodiment of this disclosure.

In another embodiment, as shown in FIG. 11, a distal end of an imaging probe 230 is fitted with a tracking fixture 232 which may include some or all of the features previously described for tracking fixtures. In this embodiment, the tracking fixture 232 includes one or more coupling mechanisms 234 located in known locations on the tracking fixture and thus in known locations with respect to the probe. In one embodiment, the coupling mechanisms are permanent magnets. One or more of these magnets may be distributed over the elongated body of the tracking fixture 232. The pose of each magnet is known with respect to the tracking fixture 232 and thus to the probe 230. A teleoperated medical instrument 236, which is similar to the instrument 102 but may have a different end effector configuration, includes a coupling feature 238. In this embodiment, the coupling feature is a permanent magnet that can grab and attach to (with unlike poles) a coupling mechanism 234. When the tracked instrument 102 is coupled to the coupling mechanism at a known and fixed pose, the pose of the probe 230 relative to the instrument can be accurately determined. A plurality of magnets allow the probe 230 to be grasped from multiple known approaches. In one embodiment, the instrument 236 may also include an active magnet that generates a temporary like pole to eject the probe 230 and tracking fixture 232 from the coupling feature 238. In any embodiment, the permanent magnet may be shielded to guide the magnetic flux. The shield may prevent the magnetic field from attracting metal objects such as staples, needles, or the like. In some embodiments, the shield may cause a stronger attraction force between the instrument and the sleeve by guiding the magnetic flux. The shield may prevent the magnetic field from interference with the probe operation. In some embodiments, a similar shield may be applied to the magnetic field of the instrument 236. In another embodiment, the coupling mechanism 234 is a suction based holder. As the instrument coupling feature 238 moves into contact with the suction based holder, a suction force is applied to secure a fixed connection.

Figure 12:
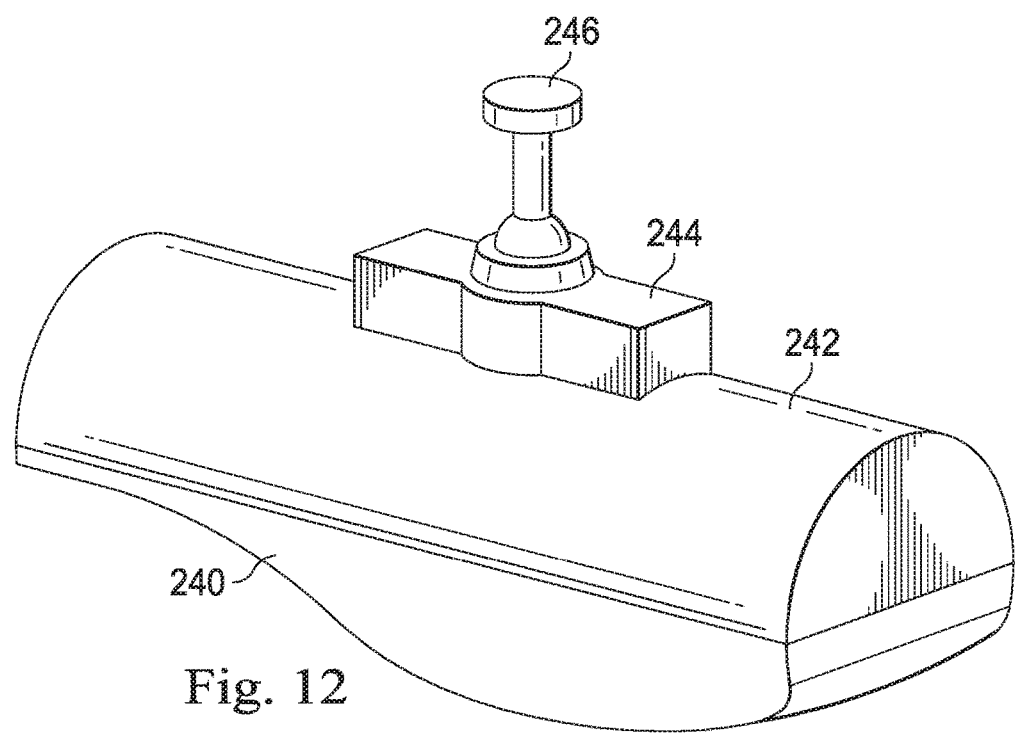
FIG. 12 illustrates a distal end of an imaging instrument with a tracking fixture according to another embodiment of this disclosure.

In another embodiment, as shown in FIG. 12, a distal end of an imaging probe 240 is fitted with a tracking fixture 242 which may include some or all of the features previously described for tracking fixtures. In this embodiment, the tracking fixture 242 includes a coupling mechanism 244. In the embodiment of FIG. 12, the coupling mechanism 244 includes a handle 246 coupled to the elongated body of the tracking fixture 242 by a compliant joint such as a ball and socket joint.

Figure 13:
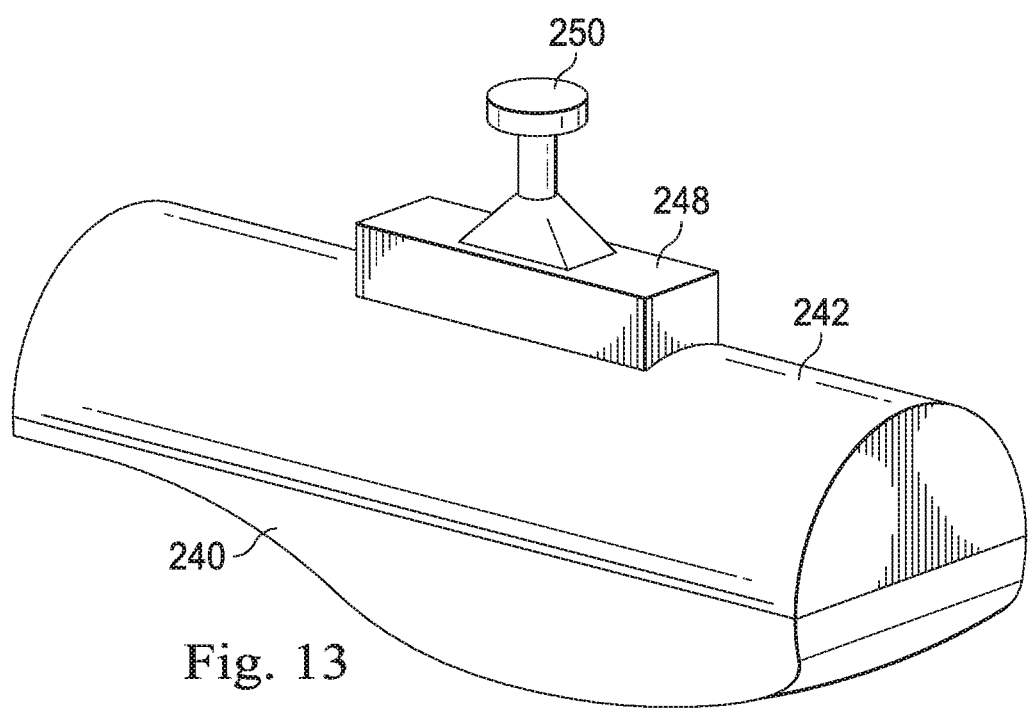
FIG. 13 illustrates a distal end of an imaging instrument with a tracking fixture according to another embodiment of this disclosure.

In another embodiment, as shown in FIG. 13, the distal end of the imaging probe 240 is fitted with a tracking fixture 242 which may include some or all of the features previously described for tracking fixtures. In this embodiment, the tracking fixture 242 includes a coupling mechanism 248. In the embodiment of FIG. 13, the coupling mechanism 248 includes a handle 250 coupled to the elongated body of the tracking fixture 242 by a compliant joint that is a flexible joint. In other embodiments, the coupling mechanism may provide a compliant joint that is a universal joint.

In either embodiment, the handles may fixedly couple to the teleoperated instrument 106 so that the pose of the instrument with respect to the handle is fixed. In some embodiments, the coupling mechanism provides a single degree of freedom, for example in the pitch angle or in the yaw angle. In other embodiments, the coupling mechanism provides movement in two degrees of freedom. In still other embodiments, the coupling mechanism provides movement in three degrees of freedom. Where the coupling mechanism provides multiple degrees of freedom, higher stiffness may be provided in some degrees of freedom and lower stiffness may be provided in other degrees of freedom. A compliant joint may provide flexibility to allow the probe to follow the surface of a curved anatomic surface (e.g. a liver surface) while the probe is being moved by the teleoperated instrument. The compliant joint allows for such movement while minimizing the instrument wrist motion.

In one embodiment, the compliant joint of the tracking fixture may include a ratcheting mechanism in selected degrees of freedom. To adjust the ratchet mechanism to achieve a desired angle between the sleeve and the holding instrument, the probe may be pushed against an instrument or an anatomic wall.

In one embodiment, a compliant joint includes an encoder mechanism to determine the relative pose of the tracking fixture and the instrument end effector. In one embodiment, a compliant joint encoder includes a permanent magnet. Magnetic field sensors on the medical instrument holding the tracking fixture may be used to determine the relative angle between the sleeve and the holding instrument. In another embodiment, the encoding mechanism includes an optical fiber shape sensor that passes through the compliant joint. Data from the shape sensor provides the bending angle of the compliant joint.

In another embodiment, the compliant joint is kinematically modeled, and the model is used to determine the relative pose between the probe and the holding medical instrument. The probe tracking may be performed using one or more sensors or by using the stereo images acquired by the endoscopic instrument.

In another embodiment, an ultrasound probe may be detachably coupled to the teleoperated medical instrument. For example, the probe may be attached and locked to the medical instrument prior to insertion into the patient anatomy. A connector used to couple the probe and the instrument may be located on or near the end effector of the instrument, near a wrist joint. In one embodiment, the probe may be connected to one jaw of the instrument. If the instrument has a second jaw, the second jaw may be used to grab and hold tissue to the primary jaw that holds the probe. The secondary jaw may include one or more sensors, such as pressure or force sensors. These sensors may be used to adjust grabbing force pressure or force to acquire consistent ultrasound images. The data from the pressure sensor may be shown to allow the clinician to visualize a pressure map and detect suspicious nodules. A pressure map may be shown in correlation with the ultrasound images to help with interpretation of the ultrasound images. The pressure map may be used to confirm judgments based on the ultrasound images. The secondary jaw may include one or more active elements. For example, the active elements may induce vibrations in the tissue and the ultrasound probe may be used to perform elastography. The active elements may induce laser pulses for photo-acoustic imaging using the detectors in the ultrasound probe. The active elements may induce RF pulses for thermo-acoustic imaging using the detectors in the ultrasound probe.

With a detachable probe coupled to an end effector of the medical instrument, a power and data cable for the probe may pass through a lumen of the medical instrument shaft. Optionally, the cable may pass around rather than through a wrist joint of the instrument. Optionally, the cable may have a flexible portion to allow for wrist motion. Optionally, all power and data signals may pass through the connector between the probe and the medical instrument. Optionally, power may pass through the medical instrument but data may be transmitted via wireless signals.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical imaging system comprising:
a teleoperated assembly including a medical instrument;
a first imaging instrument for generating a first image of a field of view of the first imaging instrument;
a second imaging instrument for generating a second image; a tracking fixture engageable along at least a portion of the second imaging instrument, the tracking fixture including one or more features wherein the medical instrument is attachable to an attachment feature of the tracking fixture to maintain a known configuration of the medical instrument relative to the second imaging instrument; and
a processor configured to determine a pose of the tracking fixture based on the one or more features of the tracking fixture and the first image.

2. The medical imaging system of claim 1 further comprising a control system of the teleoperated assembly for generating a modified second image based on information from the first image.

3. The medical imaging system of claim 1 wherein the second imaging instrument includes a set of elongated grooves and the tracking fixture includes a set of projections sized for receipt within the set of elongated grooves to attach the tracking fixture to the second imaging instrument.

4. The medical imaging system of claim 1 wherein the tracking fixture includes an expandable member.

5. The medical imaging system of claim 1 wherein the one or more features are detectable in the first image.

6. The medical imaging system of claim 1 wherein the first imaging instrument includes a camera and the second imaging instrument is an ultrasound probe.

7. The medical imaging system of claim 1 wherein the second imaging instrument includes an optical fiber shape sensor for determining a pose of the second imaging instrument.

8. The medical imaging system of claim 1 wherein a three-dimensional shape of the one or more features permits the pose of the tracking fixture to be determined based on the first image.

9. A medical imaging system further comprising:
a teleoperated assembly including a medical instrument;
a first imaging instrument for generating a first image of a field of view of the first imaging instrument;
a second imaging instrument for generating a second image;
a tracking fixture engageable along at least a portion of the second imaging instrument, the tracking fixture including one or more features configured to permit a pose of the tracking fixture to be determined, wherein the medical instrument is attachable to the tracking fixture to maintain a known configuration of the medical instrument relative to the second imaging instrument;
a guiding member rigidly coupled to the tracking fixture, the guiding member including a channel sized for receipt of a medical tool while the tracking fixture is engaged along the portion of the second imaging instrument; and
a processor configured to determine a pose of the tracking fixture based on the one or more features of the tracking fixture appearing in the first image.

10. The medical imaging system of claim 9 wherein a trajectory through the channel intersects an imaging area of the second image.

11. The medical imaging system of claim 1 wherein the tracking fixture includes a coupling mechanism for attaching the medical instrument to the tracking fixture.

12. The medical imaging system of claim 11 wherein the coupling mechanism includes a magnet.

13. The medical imaging system of claim 12 wherein the coupling mechanism includes a magnet shield.

14. The medical imaging system of claim 11 wherein the coupling mechanism includes a suction mechanism.

15. The medical imaging system of claim 11 wherein the coupling mechanism includes a compliant joint mechanism.

16. The medical imaging system of claim 15 further comprising a sensor associated with the compliant joint mechanism for determining a pose of the tracking fixture with respect to the medical instrument.

17. A medical imaging system comprising:
a stereoscopic endoscopic instrument for generating a first image;
a supplemental imaging instrument for generating a second image;
a sleeve sized to extend along at least a portion of the supplemental imaging instrument, wherein the sleeve is visible within an imaging area of the first image, the sleeve including a marking scheme visible within the first image; and
a processor configured to:
receive the first image;
determine, based on the marking scheme visible within the first image, a pose of the sleeve relative to the stereoscopic endoscopic instrument; and
modify the second image based on the determined pose of the sleeve relative to the stereoscopic endoscopic instrument.

18. The medical imaging system of claim 17 wherein the marking scheme includes a checkerboard pattern.

19. The medical imaging system of claim 17 wherein the marking scheme includes at least one of a barcode pattern, a fluorescent marker, or a light emitting device.

20. The medical imaging system of claim 17 wherein the processor is configured to modify the second image by generating a three-dimensional warped image in alignment with the first image.

* * * * *